(12) United States Patent  
Lorenz et al.

(10) Patent No.: US 9,150,493 B2  
(45) Date of Patent: Oct. 6, 2015

(54) METHOD FOR PRODUCING AROMATIC AMINES IN THE LIQUID PHASE

(75) Inventors: Wolfgang Lorenz, Dormagen (DE); Bernd Pennemann, Bergisch Gladbach (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/521,523

(22) PCT Filed: Jan. 10, 2011

(86) PCT No.: PCT/EP2011/050233  
§ 371 (c)(1),  
(2), (4) Date: Jul. 11, 2012

(87) PCT Pub. No.: WO2011/086050  
PCT Pub. Date: Jul. 21, 2011

(65) Prior Publication Data  
US 2012/0289745 A1 Nov. 15, 2012

(30) Foreign Application Priority Data  
Jan. 14, 2010 (DE) .......................... 10 2010 004 566

(51) Int. Cl.  
*C07C 211/00* (2006.01)  
*C07C 209/36* (2006.01)

(52) U.S. Cl.  
CPC .................................. *C07C 209/36* (2013.01)

(58) Field of Classification Search  
None  
See application file for complete search history.

(56) References Cited

U.S. PATENT DOCUMENTS

| | | | |
|---|---|---|---|
| 3,761,521 A | 9/1973 | Alheritiere et al. | |
| 4,792,626 A | 12/1988 | Becher et al. | |
| 5,563,296 A | 10/1996 | Zarnack et al. | |
| 5,779,995 A | 7/1998 | Witt et al. | |
| 6,350,911 B1 | 2/2002 | Sander et al. | |
| 6,894,193 B2 | 5/2005 | Zehner et al. | |
| 7,064,237 B2 | 6/2006 | Zehner et al. | |
| 7,091,383 B2 | 8/2006 | Vanoppen et al. | |
| 7,193,112 B2 | 3/2007 | Lehner et al. | |
| 7,595,424 B2 | 9/2009 | Vanoppen et al. | |
| 8,110,073 B2 * | 2/2012 | Pennemann et al. | ............ 203/14 |
| 2011/0137083 A1 | 6/2011 | Pfeffinger | |

FOREIGN PATENT DOCUMENTS

| | | | | |
|---|---|---|---|---|
| DE | 2044657 A | | 3/1972 | |
| DE | 19844901 C1 | | 11/1999 | |
| DE | 102006059678 | * | 6/2008 | ............ C07C 209/36 |
| GB | 1452466 | | 10/1976 | |
| JP | 2007231003 A | | 9/2007 | |

* cited by examiner

*Primary Examiner* — Clinton Brooks  
(74) *Attorney, Agent, or Firm* — Donald R. Palladino; Robert S. Klemz; Lyndanne M. Whalen (57) ABSTRACT

The invention relates to a process for the preparation of aromatic amines in the liquid phase by catalytic hydrogenation of the corresponding nitroaromatic compounds in at least two reaction spaces connected in series, wherein at least one reaction space is operated isothermally and at least the reaction space connected downstream thereof is operated adiabatically, and in preferred embodiments the sudden adiabatic temperature change is used for monitoring the reaction.

16 Claims, 3 Drawing Sheets

METHOD FOR PRODUCING AROMATIC AMINES IN THE LIQUID PHASE

The invention relates to a process for the preparation of aromatic amines in the liquid phase by catalytic hydrogenation of the corresponding nitroaromatic compounds in at least two reaction spaces connected in series, wherein at least one reaction space is operated isothermally and at least the reaction space connected downstream thereof is operated adiabatically, and in preferred embodiments the sudden adiabatic temperature change is used for monitoring the reaction.

It is known, for example, from EP 0 223 035 A1 that aromatic diamines such as, for example, toluoylenediamine (TDA, diaminotoluene) can be prepared by catalytic hydrogenation of the corresponding aromatic dinitro compounds. The hydrogenation is carried out with the aid of modified Raney nickel catalysts dispersed in the reaction mixture, which are then separated off by filtration or sedimentation and optionally fed back into the process. This specification focuses on the use of the modified Raney nickel catalysts. The use of a plurality of series-connected, differently operated (some isothermally, some adiabatically) reaction spaces is not disclosed therein. The hydrogenation reaction described in EP 0 223 035 A1 is very strongly exothermic. A constant problem in the hydrogenation, for example, of dinitrotoluene (DNT) to toluoylenediamine (TDA) is, therefore, the dissipation of that heat. Thus, WO 96/11052 A1 describes a reaction apparatus for carrying out sludge-phase hydrogenations using the heat of reaction to generate usable steam. Here too, the use of a plurality of series-connected, differently operated (some isothermally, some adiabatically) reaction spaces is not disclosed.

DE-OS-2 044 657 describes a process for the preparation of toluoylenediamine by hydrogenation of dinitrotoluene at elevated pressure and elevated temperature in one or two series-connected reactors, preferably high-pressure tubes, which are charged with solid bed hydrogenation catalysts containing nickel or ruthenium. When two hydrogenation reactors are used, a conversion of about 90% takes place in the first. It is not explicitly mentioned whether these reactors are to be operated isothermally or adiabatically, only that the same conditions are maintained in both reactors. The mentioned advantage of this process is the elimination of continuous separation of the catalyst. A disadvantage of this process is that a large amount of the resulting reaction mixture must be removed from the product mixture for recycling, water must be removed by distillation, and the anhydrous crude hydrogenation mixture so obtained must be fed back into the reaction.

U.S. Pat. No. 3,761,521 describes a process for the hydrogenation of aromatic nitro compounds in which the hydrogenation is carried out in a stirred container with internal cooling coils. The reactor is combined with separation of the catalyst by means of sedimentation. As a result of the density differences, the fully reacted reaction mixture circulates from the reactor into the sedimentation container, where it is decomposed into a stream that contains catalyst and a stream that is largely free of catalyst. The former is fed back into the reactor; the latter is fed to working up. If the reaction proceeds quickly enough, one reactor/sedimentation container unit is sufficient for complete reaction of the starting material. For slower reaction systems, it is recommended to connect two or more such systems in series, which requires a high outlay in terms of apparatus. In this specification too, the use of a plurality of series-connected, differently operated (some isothermally, some adiabatically) reaction spaces is not disclosed.

DE 198 44 901 C1 describes a process for the preparation of aromatic amines by the sump-phase process, in which the nitroaromatic compounds are fed into the reactor via an annular pipe with orifices. The annular pipe can also be cooled by an external heat transfer medium, in order to rule out the risk of overheating and hence thermal decomposition of the nitroaromatic compounds. Particularly good distribution of the nitroaromatic compounds in the reaction mixture is to be achieved in this process. As suitable reactors there are described, for example, loop reactors, bubble columns, preferably stirred vessels. In this specification too, the use of a plurality of series-connected, differently operated (some isothermally, some adiabatically) reaction spaces is not disclosed.

A loop reactor is described in EP 0 634 391 A1. A mixture of catalyst and DNT, reaction product that has already formed and hydrogen is mixed in a container by means of an ejector in such a manner that the reaction can take place. Important further elements are a circulating pump, a heat exchanger in the circulating stream for dissipating the heat of reaction, and a filtering unit for separating off the product stream and retaining the suspended catalyst. In this specification too, the use of a plurality of series-connected, differently operated (some isothermally, some adiabatically) reaction spaces is not disclosed.

A further process in which a loop reactor is used is described in WO 00/35852 A1. A heat exchanger is preferably integrated into the reactor in order to dissipate the heat of reaction. In addition to the loop reactor, an external circuit is described, reaction mixture preferably being removed in the lower region of the loop reactor and being fed to the upper region of the reactor again by means of a feed member. The external circuit can contain an additional heat exchanger and can be used to discharge the product while retaining the catalyst by means of for example, a gravity separator, cross-flow filter or centrifuge. The reaction procedure is described as being highly isothermal. In addition, a post-reactor can be provided in the external circuit for completing the reaction. The possible type of post-reactor is generally indicated as being of the same type as the main reactor or in the form of a stirred vessel or a flow tube. There is no indication of how a necessary post-reaction is recognised or carried out in terms of the reaction conditions. WO 00/35852 teaches that the reaction of dinitrotoluene to toluoylenediamine takes place virtually quantitatively in the main reactor and the external loop flow contains substantially pure toluoylenediamine, water and optionally solvent and catalyst. Toluylenediamine is removed from the external loop flow and fed to further working up. WO 00/35852 does not teach the use of an adiabatically operated post-reactor and monitoring of the reaction by monitoring the sudden adiabatic temperature change.

The possibility of the occurrence of unreacted nitro compounds in a reaction system as in WO 00/35852 is, however, described in DE 102 06 214 A1. DE 102 06 214 A1 teaches that, by changing the feed of the starting materials (direction of flow of at least part of the hydrogen and/or of the nitroaromatic compound in the reaction mixture upwards), the reaction of the nitroaromatic compounds takes place more completely. This is true in particular for the hydrogenation of DNT. In the process of DE 102 06 214 A1 too, the heat of reaction is dissipated at the site of its formation. This specification too does not teach the use of an adiabatically operated post-reactor and monitoring of the reaction by monitoring the sudden adiabatic temperature change.

All the processes have the disadvantage that, as well as containing the target product of the aromatic amines, the co-product water and the compounds or high molecular weight, tar-like products resulting from the known secondary reactions such as ring hydrogenations or hydrogenolytic cleavages, the reaction mixture obtained can also contain the nitroaromatic compounds used as starting materials or intermediate stages of the reaction such as nitrosoaromatic compounds. It is known that such compounds are not very stable, in particular in the presence of amines and at elevated temperature, and can decompose explosively. It must therefore be ensured that the reaction takes place completely. Conventionally, therefore, the reaction is monitored. This can take place, for example, by analysis of the product stream by gas chromatography, as described in WO 03/066571 A1. Another procedure is that of monitoring the stream of material entering into the reaction, as described in DE 102 06 214 A1.

DE 10 2005 008 613 A1 describes a process for the preparation of aromatic amines in which the contents of nitro and nitroso compounds in the reaction product are determined by means of UV-VIS absorption. DE 10 2005 008 613 A1 teaches that, in the catalytic hydrogenation of nitroaromatic compounds, the catalysts are deactivated over time. The lower the activity of the catalysts, the smaller the proportion of the starting materials converted to amines, so that the proportion of unreacted nitroaromatic compounds remaining in the reactor increases. Monitoring of the catalyst activity is therefore necessary, in particular in order to supply a sufficient amount of unconsumed catalyst to the reactor. It is also to be possible to use the process for the metering of nitroaromatic compound and fresh catalyst to the reactor system. It is a disadvantage of this process that the spectra of TDA/water mixtures with and without nitro/nitroso compounds differ only slightly, which requires complex calibrations. In addition, coatings on the measuring cells change the measuring signal, so that the calibration must be checked regularly. Gas bubbles or catalyst particles also interfere with the measurement, so that complex sample preparation is required which, in addition to the time lost between the occurrence and the detection of the effect, means not only high costs but also poor reliability of the arrangement as a whole.

WO 02/062729 A2 is concerned with improving the material exchange processes in heterogeneously catalysed hydrogenation reactions, such as, for example, the preparation of aromatic amines from the corresponding nitro compounds. By means of a specific inert gas content in the hydrogen used for the hydrogenation, a higher hydrogen saturation of the liquid phase in the reactor is to be achieved, which is to prevent increased ageing of the hydrogenation catalyst and insufficient selectivity of the reaction. The aim of this publication is ultimately also to ensure that the reaction of the nitro compound to the amine in the hydrogenation reactor is as complete as possible. The publication does not deal with the monitoring of the quality of the hydrogenation, that is to say the effect of catalyst ageing or of inadequate selectivity, or how to manage such situations.

The fundamental idea in the processes described above is either to dissipate the heat of reaction by means of heat exchangers at the site of its formation, or to take it up in a sufficiently large product stream and dissipate it at another site by means of heat exchangers in such a manner that inadmissibly high temperatures are avoided. The aim of the mentioned processes is normally, therefore, to increase the flow to heat exchangers used for heat dissipation and the thorough mixing of the in the apparatuses used for the reaction to such an extent that the temperature differences in the reaction space are as small as possible. It is additionally important for rapid hydrogenation that sufficient contents of hydrogen are present in the reaction space, which requires the introduction of gas bubbles into the reaction space and can be achieved, for example, by means of gassing stirrers, circulating-gas compressors or loop reactors. This gassing likewise leads to intensive thorough mixing of the reaction space. It is obvious that, as a result of these measures, the dwell time distribution is close to that of an ideally thoroughly mixed stirrer vessel, which is favourable to the occurrence of starting materials in the product stream and is therefore undesirable, as stated above.

EP 1 524 259 A1 (preferably nitrobenzene as starting material) and GB 1 452 466 (solely nitrobenzene as starting material) are concerned with the use of series-connected, isothermally and adiabatically operated reactors with fixed-bed catalysts in the gas-phase hydrogenation of nitroaromatic compounds. The problem of explosion prevention has for a long time not arisen in gas-phase hydrogenations to the extent as described above for liquid-phase hydrogenations (in particular of dinitroaromatic compounds). Accordingly, neither of the two specifications teaches the possibility of using the sudden temperature change in an adiabatically operated reaction space for monitoring the conversion of nitro- or nitrosoaromatic compounds. EP 1 524 259 A1 is concerned only with extending the operating time of an isothermally operated main reactor (tube bundle reactor) by a downstream, adiabatically operated reactor with a monolithic catalyst with dilution of the catalyst bed in order to moderate the reactivity of the main reactor (p. 4, l. 32-33 and l. 40). The use of monoliths is fundamental to the invention in order to avoid inadmissibly high differential pressures. Finally, in GB 1 452 466, the combination of an isothermal and an adiabatic procedure serves the purpose of better temperature monitoring (p. 3, l. 86-94). The increase in the space-time yield and in the service life are mentioned as being advantageous in this process. The process-related challenges of gas-phase hydrogenation are completely different from those of liquid-phase hydrogenation, so that the two processes are scarcely or not at all comparable.

The object of the present invention is, therefore, to provide a process for the hydrogenation of nitroaromatic compounds, in particular dinitroaromatic compounds, to the corresponding aromatic amines, in particular diamines, in the liquid phase, in which the residual content of nitroaromatic compounds (i.e. starting nitroaromatic compounds and, in the case of dinitro compounds as starting materials, in addition the aromatic mononitro-monoamine compounds formed as intermediates) and, where appropriate, of the nitrosoaromatic compounds formed as intermediate compounds (i.e. all conceivable intermediate stages containing at least one nitroso group) in the resulting crude product mixture is minimised and which permits simple and reliable monitoring of the progress of the reaction (completeness of the reaction of the nitroaromatic compounds to the aromatic amines).

Accordingly, the invention provides a process for the preparation of aromatic amines of formula (I)

in which R1 and R2 independently of one another denote hydrogen, methyl or ethyl, wherein R1 can additionally denote $NH_2$, by hydrogenation, in the presence of a catalyst, of nitroaromatic compounds of formula (II)

in which R2 and R3 independently of one another denote hydrogen, methyl or ethyl, wherein R3 can additionally denote $NO_2$, in the liquid phase in at least two series-connected reaction spaces arranged in one reactor or in a plurality of reactors, wherein
at least one reaction space is operated isothermally and at least the reaction space connected downstream thereof is operated adiabatically.

The hydrogenation of the nitroaromatic compound to the corresponding amine takes place with hydrogen or mixtures of hydrogen and inert gases as the hydrogenation reagent. Suitable catalysts are all catalysts conventional for catalytic hydrogenations. Catalysts that contain noble metals such as Pt, Pd, Rh, Ru or non-ferrous metals such as Ni, Co or Cu or mixtures thereof are preferably used. Catalysts that contain Pt, Pd, Ni or Cu are particularly preferably used, namely in the form of a suspension in water. In the case of noble metal catalysts, they are applied to supports such as, for example, activated carbon, $SiO_2$ or $Al_2O_3$; in the case of Ni catalysts, Raney-Ni can also be used. The concentration of catalyst in the reaction space is preferably from 0.01% by mass to <20% by mass, preferably from 0.5% by mass to 10% by mass, based on the total mass of the reaction mixture in the reaction space. If mixtures of hydrogen and inert gases are used, preferred inert gases are ammonia, noble gases and/or nitrogen. Hydrogen or the mixture of hydrogen and inert gases is preferably delivered in such a manner that a constant pressure is established in the reaction space, that is to say the supply of fresh hydrogenation reagent is increased as the reaction progresses (and the hydrogen is thus consumed). Where a mixture of hydrogen and inert gases is used as the hydrogenation reagent, the ratio of hydrogen to inert gas in the hydrogenation reagent that is supplied is preferably gradually increased in order to prevent the contents of the reactor from becoming depleted of hydrogen.

The reaction space is understood as being the space in which the requirements for a reaction in the liquid phase of nitroaromatic compound (or intermediate products) with hydrogen to form the desired aromatic amine are given. The reaction space is located in a technical device for carrying out chemical reactions, the reactor. Depending on the construction, the reaction space and the reactor can also be identical (e.g. in the case of bubble column reactors). The reaction space can also comprise only part of the reactor. If, for example, a liquid phase is present only in the lower region of a reactor, the gas phase located above it does not belong to the reaction space according to the invention, irrespective of the fact that, owing to the vapour pressure of the nitroaromatic compound, a—subordinate—proportion of the nitroaromatic compound may possibly enter the gas phase and react there. One reactor can also contain a plurality of reaction spaces. The reaction spaces can be in one reactor or in different reactors. Preferred reactors for the process according to the invention are stirred vessels, loop reactors, flow tubes, bubble column reactors or jet reactors.

In the process according to the invention the reaction spaces are connected in series, that is to say the product mixture from one reaction space is introduced into the following reaction space as the starting material mixture. It is possible, but not absolutely necessary, additionally to introduce fresh hydrogen, or a mixture of hydrogen and inert gases, and optionally fresh catalyst into the downstream reaction spaces. In the process according to the invention, the fresh nitroaromatic compound is introduced into only one reaction space; this is referred to as the first in the direction of flaw of nitroaromatic compound and is preferably operated isothermally. All the following reaction spaces are charged only with nitroaromatic compound that has not been reacted in the preceding reaction space. Accordingly, in the case of complete conversion in the first reaction space in the direction of flow of the nitroaromatic compound, the subsequent reaction spaces are not charged with nitroaromatic compound at all.

It is also conceivable to connect more than two reaction spaces in series, that is to say, for example, cascades such as "isothermal-adiabatic-adiabatic" (see FIG. 4), "isothermal-isothermal-adiabatic-adiabatic" or other combinations. Preferably not more than 10 reaction spaces are connected in series, particularly preferably not more than 5, most particularly preferably not more than 3, extremely particularly preferably not more than 2. Preferably, the first reaction space of a cascade in the direction of flow of the nitroaromatic compound is operated isothermally and the last reaction space of that cascade is operated adiabatically. The invention is explained in greater detail below using the embodiment with two reaction spaces connected in series. It is a simple matter for the person skilled in the art to transfer the information, if necessary, to systems having more than two reaction spaces.

Within the context of the present invention, isothermal means that at least the majority of the heat liberated by the reaction is dissipated by technical devices. Preferably, the heat of reaction is dissipated completely by technical devices. Such devices can be: tube bundle heat exchangers, coiled tubes, plate heat exchangers, Field tubes, U-tube heat exchangers. These devices are preferably accommodated in the isothermally operated reaction space. Alternatively, they can also be located outside the isothermally operated reaction space if adequate isothermy (i.e. at most a negligible temperature rise) in the reaction space is ensured by sufficiently large circulating streams.

Accordingly, adiabatic within the context of the present invention means that the heat of reaction in the adiabatically operated reaction space is not dissipated by technical devices. In adiabatic operation, the reaction space can be insulated in a particular manner against heat losses. When heat losses are negligible, the reaction enthalpy is reflected in the temperature difference between the inlet stream and the outlet stream.

Reaction in the liquid phase means that the reaction is carried out under physical conditions, in particular pressure and temperature conditions, such that the nitroaromatic compound, intermediate products and the aromatic amine are in liquid form. Preferably, absolute pressures of from 6 bar to 101 bar, preferably from 10 bar to 30 bar, and temperatures of from 50° C. to 250° C., preferably from 100° C. to 200° C., particularly preferably from 120° C. to 195° C., are maintained in all the reaction spaces. The pressure and temperature in the individual reaction spaces can be different within those ranges.

The pressure in the adiabatically operated reaction space is preferably equal to the pressure in the isothermally operated reaction space preceding it. The pressure is preferably measured in the head region of the reactor. In certain embodiments of the process according to the invention, therefore, the measurement site for the pressure is located outside the actual reaction space (for example in the gas phase above the liquid phase constituting the reaction space). The pressure so measured is not necessarily identical with the pressure in the reaction space itself but is always characteristic thereof, so that it represents a suitable reference point for relative comparisons between the pressures in different reaction spaces. The pressure in the adiabatically operated reaction space can also be slightly below the pressure in the isothermally operated reaction space. If, however, the pressure in the adiabatically operated reaction space is reduced too greatly as compared with the pressure in the isothermally operated reaction space, flash vaporisation of the reaction mixture in the feed of the adiabatically operated reaction space occurs, leading to a marked reduction in the amount of dissolved and/or dispersed hydrogen in the liquid phase. For the process according to the invention, therefore, the ratio of the pressure in an arbitrary adiabatically operated reaction space to the pressure in the isothermally operated reaction space preceding it is greater than 0.5, preferably greater than 0.7 and particularly preferably greater than 0.9.

Preferably, the temperature established in the isothermally operated reaction space by means of suitable devices for heat dissipation corresponds to the inlet temperature of the adiabatically operated reaction space connected downstream thereof.

Solvents that are inert under the reaction conditions can optionally be used, such as, for example, alcohols such as methanol, propanol, isopropanol or ethers such as dioxane, tetrahydrofuran. In order to increase the economy of the process, a low solvent concentration is generally advantageous; this will usually be from 1% by mass to <50% by mass, preferably from 20% by mass to <35% by mass, based on the total mass of the liquid phase.

Preferably, the conversion of nitroaromatic compounds and, where appropriate, of the nitrosoaromatic compounds formed as intermediate compounds in the first reaction space in the direction of flow of the nitroaromatic compound at the beginning of the hydrogenation, when the catalyst is still fresh and highly active, is 100%. As the catalyst becomes deactivated, the conversion in this reaction space will fall ever lower if no counter-measures are introduced. In the process according to the invention, the unreacted amounts of nitro- and, where appropriate, nitroso-aromatic compound are preferably reacted further, particularly preferably completely, in the adiabatically operated reaction space.

The process according to the invention is suitable in particular for the hydrogenation of DNT (in formula II: R2=methyl and R3=NO$_2$) to TDA (in formula I: R1=NH$_2$ and R2=methyl). All the isomers occur in the industrial process, but mainly 2,4-TDA and 2,6-TDA.

The process according to the invention is preferably carried out continuously. A discontinuous procedure is not ruled out, however.

In a preferred embodiment of the present invention, an adiabatically operated reaction space is connected downstream of an isothermally operated reaction space, the product mixture obtained from the isothermally operated reaction space and containing suspended catalyst being introduced into the adiabatically operated reaction space and, after further, preferably complete, reaction, being divided into two streams, one of which is freed of catalyst to the greatest possible extent and fed to further working up. Gravity separation, for example settlers, as well as filtration, for example cross-flow filters, are suitable for separating off the catalyst. The catalyst so obtained can be fed back into the isothermally operated reaction space, optionally after working-up processes. Fresh catalyst can optionally also be supplied. The other, catalyst-containing stream is fed back into the isothermally operated reaction space. The separation of water of reaction from this fed-back stream is possible but not preferred.

Transport of the reaction mixture from the isothermally operated reaction space into the adiabatically operated reaction space can take place in various ways in this embodiment, for example by pumping or under the effect of gravity by means of overflow or density differences. The same applies to the return transport of the catalyst-containing stream.

Figure 4:
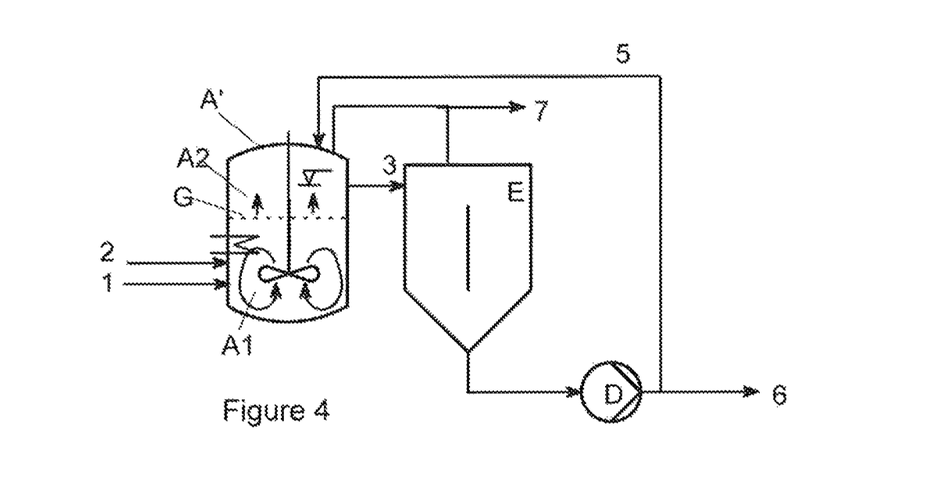

In a further embodiment, a reactor is divided into two reaction spaces by suitable flow management (see FIG. 4). The first reaction space in the direction of flow of the nitroaromatic compound is provided with a device for heat dissipation ("isothermal reaction space") and the second is not ("adiabatic reaction space"). The hydrogen, or the mixture of hydrogen and inert gases, is introduced only into the "isothermal reaction space".

The series connection according to the invention of an isothermally operated reaction space and an adiabatically operated reaction space makes use of the advantages of both procedures and is thereby particularly distinguished from the prior art in an advantageous manner. Accordingly, the majority of the conversion (preferably more than 95%, particularly preferably more than 98%, most particularly preferably more than 99%) of the starting nitroaromatic compound and of any intermediate products which may form takes place in the isothermally operated reaction space under gentle conditions, which ensure a very high degree of safety. The reaction of the residual nitroaromatic compound and of any residual intermediate products which may form under adiabatic conditions on the one hand makes use of the fact that, as a result of the higher temperatures (no heat dissipation!) in the adiabatically operated reaction space, higher conversions are possible (which is possible without risk because only a small portion of the starting nitroaromatic compound and any intermediate products which may form must be reacted) and on the other hand additionally offers the advantage of simple monitoring of the progress of the reaction, in particular of the completeness of the hydrogenation reaction of the nitroaromatic compound to the aromatic amine, by monitoring a suitable parameter which is characteristic of the part of the hydrogenation that is carried out in the adiabatically operated reaction space. Suitable parameters can be inter cilia: colour, temperature, the concentration of compounds containing nitro and nitroso groups, determined by chemical analysis, preferably by gas chromatography, or by spectroscopic analysis, preferably by UV-VIS spectroscopy. If a plurality of adiabatically operated reaction spaces are used, monitoring of this suitable parameter can be carried out for one, for a plurality or for all of the adiabatically operated reaction spaces. In a cascade comprising more than two reaction spaces, preferably at least the last reaction space is operated adiabatically and the characteristic parameter is monitored at least for that reaction space. In principle, it is also possible to monitor various parameters, for example temperature and colour.

Preferably, a critical value is calculated for each parameter by preliminary tests, for example in the case of the temperature a critical temperature which is not to be exceeded, as is described in detail below. If that previously defined critical value of that parameter is reached or exceeded, (at least) one process parameter can then be so changed that the parameter falls below the critical value again, as is explained in detail below. The critical value for the concentration of compounds containing nitro and nitroso groups is greatly dependent on the concrete boundary conditions of a production plant (e.g. temperature, pressure, nature of the nitroaromatic compound to be hydrogenated and of the catalyst used). It can be, for example, preferably at values to less than 5.0% by mass, particularly preferably to less than 2.0% by mass and most particularly preferably to less than 0.5% by mass, in each case based on the total mass of the product outlet stream of the adiabatically operated reaction space.

In preferred embodiments, the process according to the invention permits the determination of an at least qualitative, preferably quantitative relationship between particular parameters and the content of nitro-/nitroso-aromatic compounds at the inlet into and/or outlet from the adiabatically operated reaction space by laboratory tests or by engineering calculations. During the actual production, it is then possible, by monitoring one or more of those parameters, to determine when at least one process parameter must be changed in order to increase the conversion again. In this connection, the temperature in particular is the parameter of choice, as is described in detail below. The parameter colour cannot be subject to a simple quantitative description. Experienced plant operators can, however, draw qualitative conclusions at least as to the progress of the reaction on the basis of colour observations (for example at sample removal sites arranged in the product outlet stream from the adiabatically operated reaction space).

For the purpose of quantifying the relationship between particular suitable parameters and the content of nitro-/nitroso-aromatic compounds in the inlet into and/or outlet from the adiabatically operated reaction space, it can be advantageous in certain cases to prepare a calibration curve, in some circumstances a plurality of calibration curves, for various regions of pressure and temperature. If the content of nitro-/nitroso-aromatic compounds in the inlet into the adiabatically operated reaction space is chosen as the reference parameter, then, in dependence on the efficiency of the adiabatically operated reaction space, at least one process parameter is changed in good time in order to ensure that the amount of nitro-/nitroso-aromatic compounds entering the adiabatically operated reaction space can be reacted as completely as possible.

For example, the temperature $T_{adiabatic}$ measured in the adiabatically operated reaction space or in the product outlet from the adiabatically operated reaction space can be a suitable parameter. The critical value of the parameter $T_{adiabatic}$, $T_{adiabatic\ crit}$, preferably has values of from 200° C. to 250° C., depending on the other exact process conditions and the nature of the nitroaromatic compound to be hydrogenated.

The process according to the invention makes it possible to monitor the progress of the reaction (completeness of the hydrogenation reaction of nitroaromatic compound to aromatic amine), in particular also by measuring a temperature difference $\Delta T_{adiabatic}$ (sudden adiabatic temperature change) between at least one of the adiabatically operated reaction spaces and the isothermally operated reaction space preceding it. This type of reaction monitoring, which is not possible in the case of a purely isothermal procedure, is particularly preferred.

The temperature difference $\Delta T_{adiabatic}$ is preferably determined by measuring the temperature $T_{adiabatic}$
in the product outlet from the adiabatically operated reaction space or in the adiabatically operated reaction space itself
and by measuring the temperature $T_{isothermal}$
in the preceding isothermally operated reaction space or in the inlet into the adiabatically operated reaction space
and then finding the difference as follows $$\Delta T_{adiabatic} = T_{adiabatic} - T_{isothermal}.$$

If the temperature in the product outlet from the adiabatically operated reaction space is used to determine $T_{adiabatic}$, the measurement does not necessarily have to take place directly after leaving the adiabatically operated reaction space. The temperature measurement site can also be located, for example, downstream of the catalyst separation. It must simply be ensured that the measurement site provides reliable information about the evolution of heat in the adiabatically operated reaction space.

If a cascade of reaction spaces contains more than two adiabatically operated reaction spaces, it is possible, although not preferred, for a plurality of such sudden adiabatic temperature changes to be measured. For example, in a reaction space cascade of the type "isothermal (1)–adiabatic (1)–isothermal (2)–adiabatic (2)", two temperature differences, $\Delta T_{adiabatic}(1) = T_{adiabatic}(1) - T_{isothermal}(1)$ and $\Delta T_{adiabatic}(2) = T_{adiabatic}(2)(2)$, can be determined. If two adiabatically operated reaction spaces are connected directly in series, that is to say, for example, "isothermal–adiabatic (1)–adiabatic (2)", the temperature difference $T_{adiabatic}(2) - T_{isothermal}$ is preferably determined.

The "preceding" isothermally operated reaction space in this case is not the immediately preceding reaction space (which is also operated adiabatically).

The temperature measurement is carried out by means of devices known to the person skilled in the art, such as thermocouples or resistance, semi-conductor or infra-red thermometers. A suitable site for determining $T_{isothermal}$ in the isothermally operated reaction space is, for example in the case of a stirred reactor, the area close to the stirrer or, preferably, the region of the reactor wall surrounding the stirrer. A temperature so measured inside the isothermally operated reaction space is generally—if slight, unavoidable heat losses are disregarded—identical with the inlet temperature into the adiabatically operated reaction space. A suitable site for determining $T_{adiabatic}$ in the adiabatically operated reaction space is close to the reactor wall in the region of the outlet from the adiabatically operated reaction space. The temperature in the product outlet from the adiabatically operated reaction space is generally identical with the mean absolute temperature achieved as a result of the evolution of heat in that adiabatically operated reaction space (=sudden adiabatic temperature change; to be distinguished from the sudden adiabatic temperature change $\Delta T_{adiabatic}$). It is important that the measurement sites are so chosen that they are representative of the mean sudden adiabatic temperature change in the adiabatically operated reaction space and of the mean temperature in the isothermally operated reaction space.

Preferably, by means of laboratory tests, a quantitative relationship is determined between $\Delta T_{adiabatic}$ and the content of the sum of nitroaromatic compounds and, where appropriate, the nitrosoaromatic compounds formed as intermediate compounds in the product outlet of the adiabatically operated reaction space. For example, by means of a few tests it is possible to prepare a calibration curve which represents a function
$\Delta T_{adiabatic} =$
$\Delta T_{adiabatic}(c_{\Sigma(nitro-/nitroso-aromatic\ compounds,\ outlet\ adiabatic)})$;
c=concentration, preferably in % by mass.

In addition, $\Delta T_{adiabatic}$ is naturally dependent on the specific absolute temperatures and pressures that prevail.

A maximum permissible temperature difference, denoted $\Delta T_{adiabatic,\ max}$ below, is preferably also determined. This is the temperature difference which corresponds to a content of the sum of nitroaromatic compounds and, where appropriate, the nitrosoaromatic compounds formed as intermediate products in the product outlet of the adiabatically operated reaction space that is just acceptable from the point of view of both quality and explosion prevention. Such a maximum tolerable content preferably has values up to 5.0% by mass, particularly preferably up to 2.0% by mass and most particularly preferably up to 0.5% by mass, in each case based on the total mass of the product outlet stream. There is preferably further calculated a value of $\Delta T_{adiabatic}$ which is sufficiently below $\Delta T_{adiabatic,\,max}$ that, by changing at least one process parameter, the achievement of $\Delta T_{adiabatic,\,max}$ can be prevented in good time. This value is the critical value of the parameter $\Delta T_{adiabatic}$ and is denoted $\Delta T_{adiabatic,\,crit}$.

The determination of $\Delta T_{adiabatic,\,max}$ and $\Delta T_{adiabatic,\,crit}$ can be carried out on the one hand by means of tests, in which there is a sufficient amount of starting material in the feed to the adiabatically operated reaction space, or on the other hand by engineering calculations of the temperature characteristics in the adiabatically operated reaction space. The temperature difference $\Delta T_{adiabatic}$ then measured during normal production operation is compared with the maximum temperature difference $\Delta T_{adiabatic,\,max}$ and/or $\Delta T_{adiabatic,\,crit}$ so obtained.

If $\Delta T_{adiabatic}=0$, then, provided that heat losses can be disregarded, the reaction takes place completely in the isothermally operated reaction space, that is to say the conversion of nitroaromatic compounds and, where appropriate, of the nitrosoaromatic compounds formed as intermediate compounds in the isothermally operated reaction space is 100%. $\Delta T_{adiabatic}<0$ indicates heat losses as a result of imperfect insulation. $\Delta T_{adiabatic}>0$ indicates incomplete conversion in the isothermally operated reaction space.

The value of $\Delta T_{adiabatic}$ at which the change of at least one process parameter is necessary in an individual case (i.e. when $\Delta T_{adiabatic}$ becomes equal to $\Delta T_{adiabatic,\,crit}$) depends on many factors. The range within which $\Delta T_{adiabatic}$ becomes equal to $\Delta T_{adiabatic,\,crit}$ can generally assume values of from −10 K to +8 K, preferably from −8 K to +5 K, particularly preferably from −5 K to +3 K.

If a production plant is very well insulated, so that $\Delta T_{adiabatic}$ is actually 0 in the case of complete conversion in the isothermally operated reaction space, a value of $\Delta T_{adiabatic}\leq 0$ reliably indicates that no hydrogenation reaction takes place in the adiabatically operated reaction space. In such a case, values of $\Delta T_{adiabatic}$ which are only slightly greater than zero are generally still uncritical. In particularly preferred embodiments, the critical value of $\Delta T_{adiabatic}$ ($\Delta T_{adiabatic,\,crit}$) is +3 K.

On the other hand, in the case of an insufficiently insulated production plant, a value of $\Delta T_{adiabatic}\leq 0$ can falsely indicate that no reaction takes place in the adiabatically operated reaction space. In such a case, at least one process parameter must under certain circumstances be changed even at values of $\Delta T_{adiabatic}\leq 0$. Accordingly, in particularly preferred embodiments it is expedient to change at least one process parameter at values of $\Delta T_{adiabatic}\geq -5$ K (i.e. $\Delta T_{adiabatic,\,crit}$ is −5 K).

If the monitoring of one or more of the above-mentioned suitable parameters characteristic of the part of the hydrogenation that is carried out in the adiabatically operated reaction space indicates incomplete conversion in the isothermally operated reaction space, there are several possibilities:
a) Continue the reaction under constant conditions until, when a maximum permissible value of the parameter in question is reached (e.g. at $\Delta T_{adiabatic}=\Delta T_{adiabatic,\,max}$), the reaction is terminated (triggering of an alarm and/or automatic switch-off).
b) Change at least one process parameter so that the suitable parameter falls. Possible changes are, for example:
ba) supply of fresh catalyst;
bb) increase in the amount of used catalyst fed back;
bc) gradual reduction in the amount of fresh nitroaromatic compound fed in;
bd) increase in the pressure in at least one of the reaction spaces;
be) increase in the temperature in at least one of the reaction spaces.

It is preferred not to allow the amount of dissolved and dispersed hydrogen in the feed to the adiabatically operated reaction space to fall too greatly, if possible. Dispersed hydrogen is here understood as being hydrogen carried along in gas bubbles. Preferably, sufficient further hydrogen is fed into the reaction space that a constant pressure is established, and a small gas stream is removed from the gas phase of the isothermal reaction space and of the adiabatic reaction space and optionally analysed in respect of its composition (e.g. by gas chromatography). In this manner, reacted hydrogen is replaced and accumulating inert gases or gaseous reaction products are discharged.

It is important for the process according to the invention that the hydrogenation reaction in the adiabatically operated reaction space can be completed. This requires the amount of dispersed and dissolved hydrogen in the feed to the adiabatically operated reaction space to exceed the amount required for the reaction. It is known to the person skilled in the art that the amount of dissolved hydrogen is dependent on the composition of the reaction mixture, on the pressure and temperature in the isothermally operated reaction space, and on the composition of the gas phase in that reaction space. For the content of dispersed and dissolved hydrogen, gassing in the reaction space and the relative velocity of the liquid and gas phase, inter cilia, are of importance. The composition of the gas phase is determined by the partial pressures of the components in the liquid phase and their interaction with one another, the formation of gaseous secondary products such as, for example, ammonia, and the presence of impurities in the supplied hydrogen and their accumulation in the reactor.

It is also important that the liquid phase in the adiabatically operated reaction space has a sufficiently long dwell time to permit residual reaction. For the process according to the invention, the adiabatically operated reaction space has a dwell time of the liquid phase which is at least 10% of the dwell time of the liquid phase of the isothermally operated reaction space, with at least 20% and at most 300% being preferred.

The process according to the invention is particularly suitable in the case of an expected gradual and slow reduction in the rate of reaction from a state of a high rate of reaction, as is typically, but not exclusively, caused by progressive catalyst deactivation. The adiabatically operated reaction space connected downstream of the isothermally operated reaction space permits higher conversions on account of the higher temperatures (no heat dissipation!), as a result of which the catalyst deactivation is compensated for at least partially. To that end, however, the other requirements for a further continuation or the reaction, such as sufficient hydrogen and catalyst, must naturally be given. Hydrogen and catalyst can therefore optionally be metered separately into the adiabatically operated reaction space.

Working up of the product mixture freed of the catalyst first comprises separation of the water of reaction formed in the hydrogenation of the nitro groups by separation by distillation, as is known to the person skilled in the art. This is followed by separation of secondary products (e.g. partially or completely ring hydrogenated and/or deaminated and/or demethylated nitroaromatic compounds, ammonia (deamination product), optionally reaction products of the solvent (if this does not behave completely inertly), azoxy compounds, etc.). The desired aromatic amines are separated from higher boiling impurities (residue) and, if necessary, separated into their isomers. These separating operations are preferably carried out by distillation known to the person skilled in the art.

Figure 1:
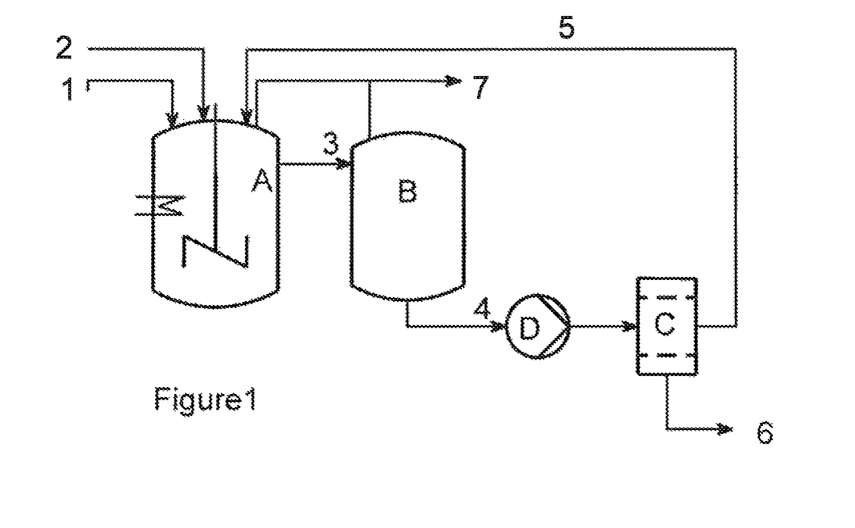

FIG. 1 shows an embodiment of the invention. Stream 1 denotes the starting material mixture to be hydrogenated (nitroaromatic compound, and optionally inert solvent). The nitroaromatic compound and the catalyst are preferably added separately; the precise location of the catalyst addition (not shown in FIG. 1) is not important for the invention. Stream 2 denotes hydrogen, A the reactor with an isothermally operated reaction space, stream 3 the reaction mixture entering the reactor B with an adiabatically operated reaction space. Stream 4 denotes the fully reacted mixture entering the filtration C (here cross-flow filter), with stream 5 the thickened mixture of reaction product and catalyst is fed back into the reactor, stream 6 denotes the reaction product, which is fed to working up, and stream 7 denotes the gas stream used for the discharge of inert gases. The pump D serves to maintain the circulation. Monitoring of the completeness of the reaction can take place, for example, by measuring the temperature difference $\Delta T_{adiabatic}$ between streams 3 and 5, 3 and 4 or 3 and 6.

Figure 2:
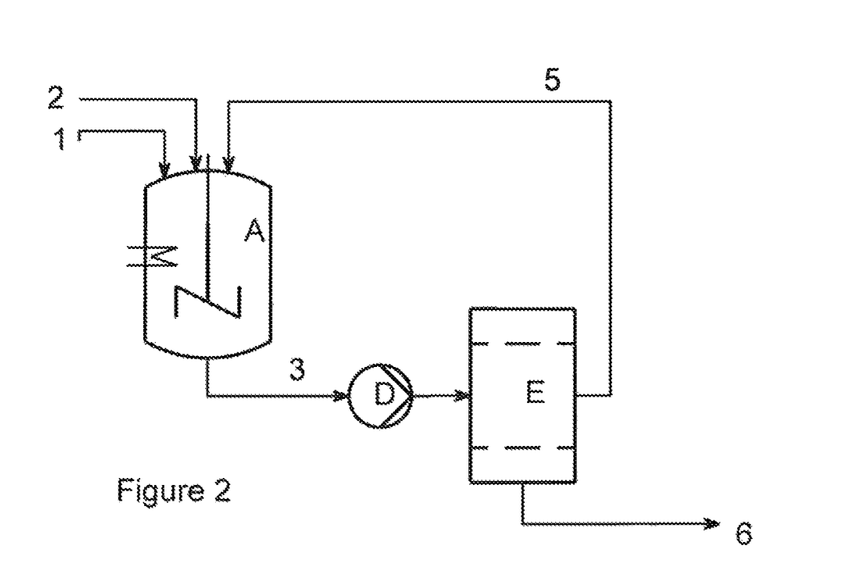

FIG. 2 shows an embodiment in which the functions of the reactor B with an adiabatically operated reaction space and the catalyst separation C are combined in one apparatus E.

Figure 3:
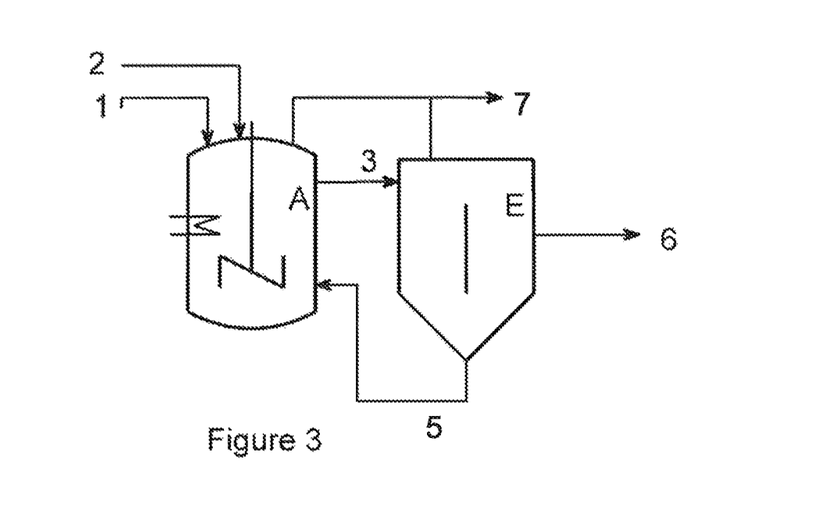

FIG. 3 describes an embodiment of the invention in which the pump D can be omitted and the feeding of the thickened reaction mixture from the apparatus E with the adiabatically operated reaction space with a device for catalyst separation (here a gravity separator) back into the reactor A with the isothermally operated reaction chamber takes place by means of the differences in density of the liquid phases.

FIG. 4 describes an embodiment in which the reactor A', which contains an isothermally operated reaction space A1, additionally also contains an adiabatically operated reaction space A2 as a result of suitable flow management. Separation of the two reaction spaces can be effected by built-in components (G), for example by sieve plates, guide plates, heat exchangers or the like. The flow in the lower region of the reactor is turbulent and evens out increasingly towards the top, in particular downstream of G. In this arrangement, the reaction space, which overall is operated adiabatically, consists of two individual adiabatically operated reaction spaces, namely the liquid reactor contents of the apparatus E and a part of the volume of the intensively gassed reactor A', specifically A2. This arrangement has the advantage that the gas supply in the first adiabatically operated reaction space (A2) is particularly high and accordingly permits the reaction of a larger amount of nitroaromatic compounds (e.g. dinitrotoluene) and accordingly also a greater adiabatic temperature difference $\Delta T_{adiabatic}$ between E and A1, which further facilitates the measurement operation. The gas bubbles introduced into A1 move through the adiabatically operated reaction space A2, so that substantially more nitro and nitroso groups can be hydrogenated than in E alone. $\Delta T_{adiabatic}$ can be determined in this arrangement by measuring the temperature close to the stirrer A1 and the temperature of the product stream 5 leaving the apparatus E.

Figure 5:
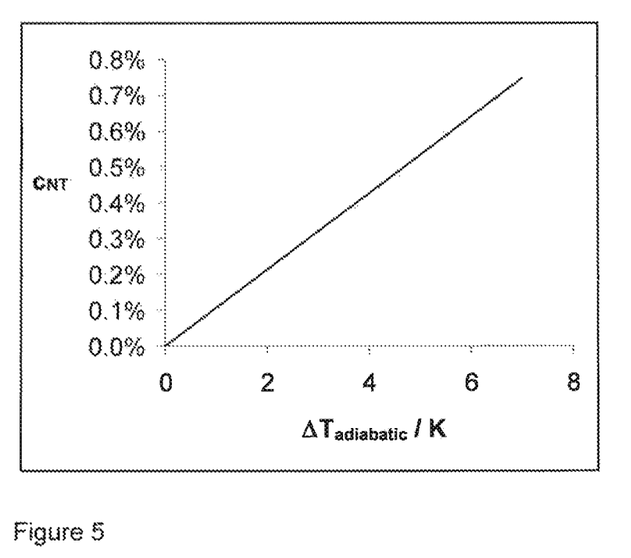

FIG. 5 shows a quantitative relationship between the sudden adiabatic temperature change of the hydrogenation of DNT and the concentration of nitrotoluidine which is present at least in the inlet stream of the adiabatically operated reaction space (see Example 2).

EXAMPLES

Example 1

According to the Invention

Dinitrotoluene (isomer mixture of 2,4-, 2,6-, 2,3-, 3,4-, 2,5-DNT) is hydrogenated in a test arrangement according to FIG. 1 consisting of a reactor A with an isothermally operated reaction space having a reaction volume of 1 liter and an internal heat exchanger, a reactor B with an adiabatically operated reaction space having a volume of 1 liter, and a device for catalyst separation consisting of a recirculating pump (D) with a frit (C). The circulating stream 5 of 2.5 l/h feeds the catalyst separated from stream 6 in the apparatus C back into the reactor A. The hydrogen stream 2 is so adjusted that an absolute pressure of 25 bar is obtained in each of the two reaction spaces. About 4 vol. % of the supplied hydrogen are conveyed away via stream 7 in order to discharge impurities and gaseous secondary products. The fully reacted mixture stream 6 is analysed by gas chromatography. Cooling water is fed through the heat exchanger, the amount of which is so adjusted that a temperature of 120° C. is established in the reaction space of A. A total of 40 g of Rany-Ni suspended in water is added as hydrogenation catalyst. The temperatures in stream 4 and in the reaction space close to the stirrer are measured, and their difference is calculated and recorded. The reaction is started by supplying a stream of 400 g/h of dinitrotoluene (1). A temperature difference $\Delta T_{adiabatic}$=T (4)–T(A, stirrer)=–1 K is measured (i.e. no reaction takes place in B), while no nitroaromatic compounds can be detected in stream 6 by means of gas chromatography. The reaction is carried out under otherwise constant conditions until the temperature difference $\Delta T_{adiabatic}$ has risen to +8 K (i.e. the DNT is no longer being reacted completely in A). This is achieved after 360 hours. The reaction is then terminated and a content of 3.8% by mass of nitrotoluidine is found in stream 6.

Example 2

According to the Invention

The relationship shown in FIG. 5 between $\Delta T_{adiabatic}$=T (4)–T(A, stirrer) and the concentration of the intermediate product nitrotoluidine found in the stream 3 to the adiabatically operated reaction space ($c_{NT}$; given in % by mass, based on the total mass of stream 3) is determined by means of the heat of reaction for the hydrogenation reaction and the heat capacity of the mixture formed in the reaction of Example 1. $c_{NT}$ represents the minimum concentration of nitrotoluidine, assuming perfect heat insulation. The relationship shown in FIG. 5 is further based on the assumption that sufficient hydrogen for the complete reaction of nitro groups is always present in the adiabatically operated reaction space. Data required for the preparation of FIG. 5 (or comparable diagrams) can be taken, for example, from the databank DIPPR known to the person skilled in the art. At $\Delta T_{adiabatic} \geq +3$ K, fresh catalyst is added in order to ensure that the adiabatically operated reaction space is not overloaded.

Example 3

According to the Invention

In the arrangement of Example 1, 15 g of catalyst, suspended in water, are weighed and the reaction is started.

Whenever $\Delta T_{adiabatic}$ exceeds a value of 1 K, 3 g of catalyst are added. The reaction product leaving the adiabatically operated reaction space (stream 4) is tested by gas chromatography at regular intervals; DNT, nitrotoluidine and nitroso compounds are not found.

What is claimed is:

1. A process for the production of an aromatic amine represented by formula (I)

(I)

in which

R1 and R2 independently of one another represent hydrogen, a methyl group or ethyl group, and wherein R1 can additionally represent $NH_2$, comprising hydrogenating a nitroaromatic compound represented by formula (II)

(II)

in which

R2 and R3 independently of one another represent hydrogen, a methyl group or ethyl group, and wherein R3 can additionally represent $NO_2$, in the presence of a catalyst in the liquid phase in at least two series-connected reaction spaces arranged in one reactor or in a plurality of reactors, wherein at least one reaction space is operated isothermally and at least one reaction space connected downstream thereof is operated adiabatically.

2. The process of claim 1 in which progress of the hydrogenation reaction is determined by monitoring a characteristic parameter of the hydrogenation carried out in at least one adiabatically operated reaction space the characteristic parameter being selected from color, temperature, and concentration of compounds having nitro or nitroso groups.

3. The process of claim 2 in which at least one process parameter is changed when the characteristic parameter has reached or exceeded its critical value so that the characteristic parameter falls below the critical value.

4. The process of claim 3 in which the characteristic parameter is the temperature $T_{adiabatic}$ measured in at least one adiabatically operated reaction space.

5. The process of claim 3 in which the characteristic parameter is the temperature $T_{adiabatic}$ measured in the product outlet from at least one adiabatically operated reaction space.

6. The process claim 4 in which the critical value of the parameter $T_{adiabatic}$ is from 200° C. to 250° C.

7. The process claim 5 in which the critical value of the parameter $T_{adiabatic}$ is from 200° C. to 250° C.

8. The process of claim 3 in which the process parameter changed is at least one of the following:
a) supply of fresh catalyst is adjusted;
b) amount of used catalyst supplied is increased;
c) amount of fresh nitroaromatic compound fed to the hydrogenation reaction is gradually reduced;
d) pressure in at least one of the reaction spaces is increased; or
e) temperature in at least one of the reaction spaces is increased.

9. The process of claim 2 in which the concentration of compounds containing nitro and nitroso groups is determined by chemical or spectroscopic analysis.

10. The process of claim 2 in which the characteristic parameter is the temperature difference $\Delta T_{adiabatic} = T_{adiabatic} - T_{isothermal}$ between at least one adiabatically operated reaction space and the isothermally operated reaction space preceding it, and $T_{adiabatic}$ is measured in the adiabatically operated reaction space product outlet or in the adiabatically operated reaction space and $T_{isothermal}$ is measured in the preceding isothermally operated reaction space or in the adiabatically operated reaction space inlet.

11. The process of claim 10 in which the critical value of the parameter $\Delta T_{adiabatic}$ ($\Delta T_{adiabatic, crit.}$) is from −10 K to +8 K.

12. The process of claim 1 in which temperatures of from 50° C. to 250° C. and absolute pressures of from 6 bar to 101 bar are maintained in all the reaction spaces.

13. The process of claim 12 in which the ratio of the pressure in an arbitrary adiabatically operated reaction space to the pressure in the isothermally operated reaction space preceding it is greater than 0.5.

14. The process of claim 1 in which dinitrotoluene (in formula II: R2=methyl and R3=$NO_2$) is hydrogenated to produce toluenediamine (in formula I: R1=$NH_2$ and R2=methyl).

15. The process of claim 1 in which from 2 to 10 reaction spaces are connected in series.

16. The process of claim 1 in which the first reaction space in the direction of flow of the nitroaromatic compound is operated isothermally and the last is operated adiabatically.

* * * * *